United States Patent [19]
Taylor et al.

[11] Patent Number: 6,136,591
[45] Date of Patent: Oct. 24, 2000

[54] BIORESOLUTION OF N-ACYLAZETIDINE-2-CARBOXYLIC ACIDS

[75] Inventors: Stephen John C. Taylor, Isleham; Julian Simon Parratt, Waterbeach, both of United Kingdom

[73] Assignee: Astra AB, Sodertalje, Sweden

[21] Appl. No.: 09/202,431

[22] PCT Filed: Jul. 15, 1997

[86] PCT No.: PCT/GB97/01916

§ 371 Date: Dec. 15, 1998

§ 102(e) Date: Dec. 15, 1998

[87] PCT Pub. No.: WO98/02568

PCT Pub. Date: Jan. 22, 1998

[30] Foreign Application Priority Data

Jul. 15, 1996 [GB] United Kingdom .................. 9614856

[51] Int. Cl.[7] .............................. C07C 1/04; C12P 13/04; C12P 17/10
[52] U.S. Cl. ............................................. 435/280; 106/121
[58] Field of Search ..................................... 435/106, 121, 435/280

[56] References Cited

FOREIGN PATENT DOCUMENTS 94 00593   6/1994   WIPO .

OTHER PUBLICATIONS

C.R. Johnson et al.: "Enzymic asymmetrization of meso–2–cycloalken–1, 4–diols and their diacetates in organic and aqueous media" Tetrahedron Letters, vol. 33, No. 48, 1992, pp. 7287–7290.

R.M. Rodebaugh et al.: "Resolution of DL–Azetidine–2–carboxylic acid" Journal of Heterocyclic Chemistry, vol. 6, No. 6, 1969, pp. 993–994.

*Primary Examiner*—Sandra E. Saucier
*Attorney, Agent, or Firm*—Nixon & Vanderhye

[57] ABSTRACT

Process for obtaining an enantiomerically enriched N-acylazetidine-2-carboxylic acid, wherein a racemic N-acylazetidine-2-carboxylic acid ester is contacted with an enzyme that displays enantiospecificity to form enantiomerically enriched N-acylazetidine-2-carboxylic acid.

18 Claims, No Drawings

BIORESOLUTION OF N-ACYLAZETIDINE-2-CARBOXYLIC ACIDS

FIELD OF THE INVENTION

This invention relates to a novel resolution method which is useful in the production of enantiomerically-pure azetidine-2-carboxylic acid, especially enantiomerically-pure (S)-azetidine-2-carboxylic acid.

BACKGROUND OF THE INVENTION

Azetidine-2-carboxylic acid is an unusual amino acid, the (S)-enantiomer of which is known to be useful in the synthesis of inter alia high molecular weight polypeptides, and in particular as an analogue of the well known amino acid proline.

This amino acid is of limited availability from natural sources, and in nature is found only as the (S)-enantiomer. The development of an efficient and economic synthetic method for producing both the pure racemic compound and either of the individual (R)- or (S)-single enantiomers is therefore desirable.

Previously documented chiral syntheses of (S)-azetidine-2-carboxylic acid include a five step preparation via homoserine lactone, starting from N-tosyl protected L-methionine (see for example Japanese Patent Application N° 14457/74 and Bull. Chem. Soc. Jpn. (1973) 46, 699) and a five step preparation via L-4-amino-2-chlorobutyric acid, starting from L-2,4-diaminobutyric acid (see Biochem. J. (1956) 64, 323).

Previously documented preparations of enantiomerically-pure azetidine-2 -carboxylic acid from the racemate involve long and relatively complicated multi-step methodology.

For example, a four step preparation involving the protection, resolution and subsequent deprotection of racemic azetidine-2-carboxylic acid is known from J. Heterocyclic Chem. (1969) 6, 993. In this method, N-carbobenzyloxy-protected racemic azetidine-2-carboxylic acid is resolved using L-tyrosine hydrazide as resolution agent, and then isolated before a final deprotection step. This process has the further disadvantage that L-tyrosine hydrazide is expensive.

Such methods present the problem that they are typically cumbersome because of the need to recycle the resolving agent and inevitably only produce half of the material as the required isomer. For an economic overall process it thus becomes necessary to find a method for the recycling of the unwanted isomer, and for this to be integrated into a process with the minimum of extra chemical steps.

Moreover, racemic azetidine-2-carboxylic acid obtained via chemical synthesis inevitably contains contaminants. Thus a resolution procedure which produces only the required single enantiomer, as well as being more economic, is also expected to facilitate chemical purification of the product.

Bioresolution is a procedure which is known to be of use generally in the production of enantiomerically-pure compounds. However, the potential utility and effectiveness of the technique in the resolution of a particular chiral compound is difficult to predict.

No biocatalytic resolution method has been previously disclosed for azetidine-2-carboxylic acid. Moreover, no resolution has been disclosed for azetidine-2-carboxylic acid which integrates recycling of the unwanted isomer in an efficient manner and which takes account of impurities arising from the racemate synthesis.

We have now surprisingly found that enantiomerically enriched azetidine-2-carboxylic acid may be obtained in an extremely enantiomerically-pure form, and in extremely high yields, via a novel and efficient bioresolution process.

DESCRIPTION OF THE INVENTION

According to the invention there is provided a process for obtaining an enantiomerically enriched N-acylazetidine-2-carboxylic acid, which process comprises the biotransformation of a racemic N-acylazetidine-2-carboxylic acid ester with an enzyme that displays enantiospecificity (hereinafter referred to as "the process according to the invention").

The term "enantiomerically enriched" when used herein means any mixture of the enantiomers of an N-acylazetidine-2-carboxylic acid in which one enantiomer is present in a greater proportion than the other, for example mixtures with an enantiomeric purity (enantiomeric excess; e.e.) of greater than 50%, preferably at least 70% and more preferably at least 90%.

Persons skilled in the art will be aware that the process according to the invention may also be referred to as a process for obtaining an "optically enriched" N-acylazetidine-2-carboxylic acid.

The process according to the invention comprises the use of an appropriate enzyme to preferentially hydrolyse one enantiomer of an N-acylazetidine-2 -carboxylic acid ester to the corresponding acid, which acid may be readily separated from the other, unwanted, enantiomeric ester and from impurities arising from the synthesis of the racemic N-acylazetidine-2-carboxylic acid ester. Moreover, the remaining ester may be readily recovered, racemized and re-used in the resolution process.

Esters of N-acylazetidine-2-carboxylic acids which may be used in the process according to the invention include aryl (e.g. phenyl) or linear or cyclic alkyl (especially lower alkyl (e.g. $C_{1-6}$ alkyl)) esters. Particular esters which may be mentioned include propyl, ethyl and especially methyl esters of N-acylazetidine-2-carboxylic acids.

N-Acyl groups of N-acylazetidine-2-carboxylic acids, and esters, which may be used in the process according to the invention include linear or cyclic alkanoyl or optionally-substituted benzoyl groups. However, we prefer the N-acyl group to be an optionally substituted N-benzoyl group, and particularly a N-benzoyl group.

The process according to the invention may be carried out in the presence of a suitable solvent which does not interfere with the resolution process. Suitable solvents include water, which may be buffered to a suitable pH using a suitable buffer system including those commonly used in biological systems (e.g. buffers such as Tris, MESm, Bis-Tris, ACES, PIPES, MOPSO) and inorganic buffers such as phosphate buffers.

The biotransformed acid and ester may be separated in accordance with techniques which are well known to those skilled in the art, for example by solvent extraction.

The N-acyl group of the biotransformed enantiomerically enriched acid may subsequently be removed in order to produce enantiomerically pure azetidine-2-carboxylic acid in accordance with techniques which are well known to those skilled in the art, for example by hydrolysis in the presence of alkali. Saponification may be carried out in this way in aqueous media, at between room temperature and 100° C., in the presence of an appropriate alkali (e.g. an alkali metal hydroxide, such as lithium, sodium or potassium hydroxide). We have found, advantageously, that saponification of the enantiomerically enriched N-acylazetidine-2-carboxylic acid (and, in particular, the N-benzoyl derivative) proceeds without racemization.

The process according to the invention may thus be used as part of a process to produce enantiomerically enriched azetidine-2-carboxylic acid.

According to a further aspect of the invention there is provided a process is for preparing an enantiomerically-pure azetidine-2-carboxylic acid, which comprises carrying out a biotransformation as hereinbefore described, followed by deacylation of the resultant enantiomerically enriched N-acylazetidine-2-carboxylic acid.

Although the process according to the invention may be used in the production of either enantiomer of azetidine-2-carboxylic acid with an enantiomeric purity (enantiomeric excess; e.e.) of greater than 80%, by "enantiomerically pure azetidine-2-carboxylic acid" we mean an enantiomer of azetidine-2-carboxylic acid with an e.e. of greater than 50%.

Enantiomeric purity may be further improved (for example to greater than 98%) by crystallisation from an appropriate solvent (e.g. ethyl acetate) which at the same time increases chemical purity.

Racemization of the remaining, non-biotransformed yet enantiomerically enriched, ester may take place by treatment with an appropriate base (e.g. sodium methoxide) in the presence of an appropriate solvent (e.g. methanol) at, for example, between 20 and 100° C. (depending on the solvent employed). The re-racemized ester may subsequently be re-used in the process according to the invention.

By employing a suitable enzyme, the process according to the invention may be used, in conjunction with a deacylation step, to produce enantiomerically pure (R)- or enantiomerically pure (S)-azetidine-2-carboxylic acid. However, in view of the aforementioned utility of the (S)-enantiomer we prefer that the process according to the invention is used in the production of the latter, and that the enzyme has enantiospecificity for the (S)-ester.

In particular, we have found that an efficient process to (S)-azetidine-2-carboxylic acid may be effected through bioresolution of a racemic N-benzoylazetidinecarboxylic acid alkyl ester using an appropriately enantiospecific enzyme followed by removal of the N-benzoyl group.

Enzymes for use in the process according to the invention may be used in the presence of the organism from which it originates or in an isolated form. The enzyme may be immobilised if desired.

The selection of a suitable enzyme system may proceed by way of a suitable protocol comprising the attempted biotransformation of a racemic N-acylazetidine-2-carboxylic acid ester in the presence of a test enzyme, for example as described hereinafter.

The term "attempted biotransformation" when used herein means providing a racemic N-acylazetidine-2-carboxylic acid ester in the presence of a suitable quantity of test enzyme, and determining whether or not an enantiomerically enriched N-acylazetidine-2-carboxylic acid (as defined hereinbefore) is formed. Resolution conditions may be varied as described hereinbefore and the enantiomeric purity of the product determined in accordance with techniques which are well known to those skilled in the art, such as those described hereinafter.

Thus, according to a further aspect of the invention there is provided a method of selection of an enzyme for use in the process according to the invention which comprises the attempted biotransformation of a racemic N-acylazetidine-2-carboxylic acid ester in the presence of a test enzyme.

Examples of suitable enzymes for use in the process according to the invention include those with properties characteristic of (and/or having the same enzymatic activity as) *Candida antarctica* lipase and *Aspergillus tamarii* esterase. We have found that such enzymes preferentially hydrolyse the (S)-ester to the (S)-acid, which may be easily separated from the unwanted (R)-ester by extraction, and subsequently saponified a hereinbefore described. By using the term "enzymes with properties characteristic of" an enzyme from an organism, we are including enzymes which originate both directly and indirectly from the original organism, for example enzymes which are expressed from the relevant gene in a suitable heterologous host organism.

It will also be clear to those skilled in the art that an alternative route to the production of (S)-azetidine-2-carboxylic acid from racemic N-acylazetidine-2-carboxylic acid ester may involve the enzymatic production of (R)-N-acylazetidine-2-carboxylic acid using an appropriately enantiospecific enzyme (leaving the (S)-ester unconverted), followed by separation as indicated above. The (R)-azetidine-2-carboxylic acid may then be racemized and esterified, in either order, to provide further racemic substrate. The ester and N-acyl groups of the (S)-ester may subsequently be removed in accordance with conventional procedures, in one or two steps, in order to produce to (S)-azetidine-2-carboxylic acid. However, in view of the number of steps involved, this procedure is less preferred than the direct enzymatic hydrolysis of the (S)-ester to the (S)-acid.

The process according to the invention has the advantages that, unlike the chemical methods described hereinbefore, it avoids the need to handle stoichiometric amounts of resolving agents or auxiliaries; the products from the biotransformation are easily separable; and it provides the materials in a form where the unwanted enantiomer can be readily recycled. Moreover, the process according to the invention has the advantage that enantiomerically pure azetidine-2-carboxylic acid may be prepared in higher yields, with greater enantiomeric purity, in a manner which involves fewer steps, in less time, more conveniently and at a lower cost than processes previously employed for the production of enantiomerically pure azetidine-2-carboxylic acid.

EXAMPLES

Example 1

Resolution of Racemic N-Benzoylazetidine-2-carboxylic Acid Methyl Ester

The ester (4.8 g, 21.9 mmol) was stirred in buffer solution (pH 7.5, 50 mM potassium phosphate, 100 mL) at room temperature. Lipase from *Candida antarctica* (0.48 g; Chirazyme L2; Boehringer Mannheim) was added and the mixture titrated to pH 7.5 using 1M NaOH. When base uptake showed 38% conversion after 3.5 hours, the enzyme was removed by filtration, and the pH adjusted to 8.5 with 5M NaOH. The ester was extracted with ethyl acetate (300 ml, 5 times), then the combined organic solutions washed with saturated sodium bicarbonate solution (100 ml), brine (100 ml), dried over $MgSO_4$, then filtered and evaporated in vacuo to yield a colourless oil (7.72 g, 57% e.e., determined by chiral GC: Chirasil DEX CB column) for racemization. The acid product was recovered by acidification of the biotransformation solution to pH 1.6, followed by extraction with ethyl acetate (200 ml, 4 times). The resulting solution was dried over $MgSO_4$, then evaporated to dryness to give a viscous oil (1.7 g, 84% e.e., determined by derivatization to the corresponding methyl ester and subsequent chiral GC analysis as above).

(S)-N-Benzoylazetidine-2-carboxylic acid (1.6 g, 84% e.e.) was stirred in 4M NaOH solution (100 ml) for 18 hours at ambient temperature followed by 3.5 hours at 75° C. After cooling to 4° C. and acidification to pH 1.5, the solution was extracted with ethyl acetate (250 ml) then evaporated to dryness to give a white solid (1.11 g). This was dissolved in water (100 ml) then Amberlite IRA-67 added (4 g). The reaction was stirred at room temperature, then the resin removed by filtration, and the filtrate evaporated in vacuo to yield the free amino acid as a white solid (0.90 g). The product was crystallized to 98% e.e., by reflux in methanol for 15 minutes, followed by crystallization at 4° C., to give (S)-azetidine-2-carboxylic acid as a white solid (0.39 g, 98% e.e., determined by chiral HPLC: Chirex (D) Penicillamine column).

Example 2
Crystallization of Enantiomerically Enriched N-Benzoylazetidine-2-carboxylic Acid (S)-N-Benzoylazetidine-2-carboxylic acid (10.0 g, 48 mmol, 70% e.e.) was stirred with ethyl acetate (20 ml) at room temperature for 10 minutes before being cooled on an ice bath for 2 hours. The white solid produced (4.09 g, >98% e.e.) was collected by suction filtration and dried at the pump for 15 minutes.

Example 3
Racemization of N-Benzoylazetidine-2-carboxylic Acid Methyl Ester (S)-N-Benzoyl-2-azetidinecarboxylic acid methyl ester (5.2 g, 23.7 mmol, 98% e.e.) was dissolved in methanol (200 ml), then sodium methoxide (0.26 g, 4.8 mmol) added and the solution refluxed for 24 hours. Acetic acid was added until the pH was 6.5, and the solvents removed by evaporation. The residues were dissolved in ethyl acetate (400 ml), extracted with water (100 ml), then brine (100 ml). The ethyl acetate layer was dried ($MgSO_4$) and evaporated in vacuo to give a colourless liquid (4.5 g) of 5% e.e.

Example 4
Biotransformation of N-Benzoylazetidine-2-carboxylic Acid Methyl Ester by *Candida antarctica* Lipase under High Ionic Strength The title ester (110 g crude) was stirred in buffer solution (1M $KH_2PO_4$, pH 7.0, 600 mL) and methyl t-butylether (200 mL) at 25° C. Lipase from *Candida antarctica* (22 g; Chirazyme L2; Boehringer Mannheim) was added and the mixture stirred for 24 hours. The enzyme was removed by filtration, then the methyl t-butylether allowed to separate. The aqueous layer was extracted twice with ethyl acetate (250 mL), then all the organic layers were combined and the solvents removed in vacuo. This yielded 47 g of a yellow oil containing the residual esters. The aqueous layer was acidified to pH 2.5 with concentrated HCl then extracted 5 times with ethyl acetate (250 mL). The ethyl acetate fractions were combined and evaporated in vacuo to a damp cake, then the resulting white crystalline solid was thoroughly mixed with a 3:1 solution of heptane:ethyl acetate (50 mL). The crystalline product was filtered then dried to yield 37.2 g of 97.7% e.e. (S)-N-benzoylazetidine carboxylate. (The e.e. was determined as described in Example 5 below.)

Example 5
Identification of an Esterase-Containing *Aspergillus tamarii* Strain by Screening Selected microbial strains with known esterase activity (obtained from the applicant's strain collection) were grown in a medium consisting of an aqueous solution of $KH_2PO_4$ (7 g/L), $K_2HPO_4$ (2 g/L), $(NH_4)_2SO_4$ (1 g/L), yeast extract (10 g/L), a trace elements solution (1 ml/L) and glucose (10 g/L). The medium was made up at 25 mL per 250 mL Erlenmeyer flask, and was adjusted to pH 6.0 (for fungi and yeasts) and pH 7.0 (for bacteria) prior to sterilisation at 121° C. for 20 minutes. The trace elements solution consisted of $CaCl_2.2H_2O$ (3.6 g/L), $CoCl_2.6H_2O$ (2.4 g/L), $CuCl_2.2H_2O$ (0.85 g/L), $FeCl_3.6H_2O$ (5.4 g/L), $H_3BO_4$ (0.3 g/L), HCl (333 mL (conc. HCl)/L), $MnCl_2.4H_2O$ (2.0 g/L), $Na_2MoO_4.2H_2O$ (4.8 g/L), and ZnO (2.0 g/L). 100 μL of glycerol stock of each strain was inoculated into the flasks and grown at 25° C. in a New Brunswick controlled environment incubator shaker (Model No. G-25) at 250 rpm for 24 to 72 hours. 10 mL samples of each culture were then harvested by centrifugation and the pellets resuspended in 4 mL 50 mM $KH_2PO_4$, pH 7.0.

In a scintillation vial 860 μL of 50 mM $KH_2PO_4$, pH 7.0 was mixed with 40 μL of 50% w/v N-benzoylazetidine-2-carboxylic acid methyl ester (2.0 g N-benzoyl-2-azetidinecarboxylic acid methyl ester, +2 mL $H_2O$, +0.02 g Tween 80, sonicated at 15–18 μm at 4° C. for 10 minutes at 10 seconds on and 3 seconds off) and 100 μL of re-suspended culture, grown as described above. Reactions were carried out in a New Brunswick controlled environment incubator shaker (Model No. G-25) at 25° C., 250 rpm. Samples were taken over up to 7 days and assayed for conversion by HPLC. Thus, samples were diluted, as appropriate, and 20 μL injected onto a 5 cm Hypersil BDS C18 column. The elution buffer was 50% v/v MeOH+1 g/L $H_3PO_4$. Flow rate was 1.5 mL.min$^{-1}$ and detection was at 225 nm, with a run time of 3 minutes. For those reactions showing significant hydrolysis, e.e.s of the ester and product were determined. The e.e. of the ester was determined by GC. The pH of the samples was adjusted to pH 9.5 with NaOH and extracted into ethyl acetate, dried with $Mg_2SO_4$ and injected onto a 25 m, 0.25 mm CHIRASIL DEX CB column. The oven temperature was maintained at 125° C. during the analysis. The e.e. of the product was determined by HPLC. The pH of the samples was adjusted to pH 9.5 with NaOH and extracted four times into ethyl acetate to remove the ester. The pH was then adjusted to 1.5 with $H_3PO_4$ and the product extracted into ethyl acetate, dried with $Mg_2SO_4$, and 20 μL injected onto a 25 cm Chiralcel OD column. The elution buffer was 92:8:1 heptane:propan-2-ol:trifluoroacetic acid. The flow rate was 1.0 mL.min$^{-1}$ and detection was at 254 nm. Of the strains employed, one, *Aspergillus tamarii*-CMC 3242, in the initial screen achieved 30% conversion of the added substrate after 48 hours biotransformation. The residual ester was shown to be the (R)-enantiomer with a e.e. in excess of 99% and the product to be the (S)-enantiomer with an e.e. in excess of 74%. The, *Aspergillus tamarii*-CMC 3242 strain was deposited on Jul. 8, 1997 at the International Mycological Institute (Egham, UK), under the terms of the Budapest treaty, and has been given the accession number IMI 375930.

Example 6
Fermentation of *Aspergillus tamarii*-CMC 3242

For preparation of spore suspension inoculum, a culture of *Aspergillus tamarii* was spread plated onto a PDA plate (39 g/L potato dextrose agar (Oxoid CM139) sterilised at 121° C. for 20 minutes, cooled to 50° C. and poured into 140 mm petri dishes) and incubated at 25° C. for 7 days. The spores of *Aspergillus tamarii* were then resuspended in sterile (sterilised at 121° C. for 20 minutes) 10% w/v glycerol+0.1% w/v Tween 80. 1 mL samples were aliquoted into 2 mL cryovials and stored at −80° C. The following medium was used in the fermenters: $KH_2PO_4$ (7 g/L), $K_2HPO_4$ (2 g/L), $(NH_4)_2SO_4$ (1 g/L), $MgSO_4.7H_2O$ (1 g/L), Trace elements solution (1 mL/L), polypropylene glycol (1 mL/L), yeast extract (20 g/L), and sucrose (20 g/L). The media was made up to a final volume of 1.5 L per fermenter and the pH adjusted to 6.0 prior to sterilisation (60 minutes at 121° C.). The sucrose was sterilised separately as a 50% w/v solution and added to the fermenter after cooling. The fermenter was inoculated with the 1 mL of the spore suspension. The temperature was maintained at 25° C. and pH controlled between 5.8 and 6.2. Agitation was 1000 rpm and air flow set at 1.0 L/min. A feed of 100 mL 34% w/v sucrose, +100 mL 34% w/v yeast extract, +1.7 g/L $(NH_4)_2SO_4$ (sterilised separately at 121° C. for 60 minutes) was added to the fermenters after 48 hours. The fermenters were harvested after 72 hours growth by filtration and stored as a cell paste at −20° C. A total wet biomass of 250 g was collected, with an activity of 41.7 $U.g^{-1}$ of cells (1 U=1 mg product produced in 1 hour).

Example 7

Whole Cell Biotransformation of N-Benzoylazetidine-2-carboxylic Acid Methyl Ester by *Aspergillus tamarii* and Isolation of (S)-Azetidine-2-carboxylic Acid Frozen cell paste (50 g) was thawed in 200 mL 0.1M $Na_2HPO_4/NaH_2PO_4$ buffer, pH 6.4. The cells were disrupted using a mortar and pestle. 100 g of racemic N-benzoylazetidine-2-carboxylic acid methyl ester was added to the reaction and the volume made up to 1000 mL with 200 mL 0.1M $Na_2HPO_4/NaH_2PO_4$ buffer, pH 6.4. The reaction was run at 25° C. and pH controlled at 6.4. A further 50 g of cells was added after 4.5 hours. After 12 hours, the biotransformation broth was filtered through a Celite pad. The residues were washed with dichloromethane (500 mL), the biphasic filtrate partitioned and the aqueous solution extracted with further dichloromethane (4×750 mL). The combined dichloromethane solutions were washed with brine (200 mL), dried ($MgSO_4$), filtered and the solvent evaporated in vacuo to yield an orange oil (56.1 g, 56.1% recovery, 54% e.e.). The original aqueous solution was acidified (pH2, c.HCl) and extracted again with dichloromethane (3×750 mL). The organic (lightly emulsified) solutions were separated each time and combined. These combined extracts separated out on standing (1 hour) and were put through a separating funnel. The organic layer was washed with brine (100 mL), dried ($MgSO_4$), filtered and the solvent evaporated in vacuo to yield a semi-crystalline solid (33.7 g; 36% yield; 94% e.e.). The semi-crystalline acid (33 g) was stirred in ethyl acetate (75 mL) for a total of 20 minutes at room temperature and the white solid (18 g; 55% yield; >99% e.e.) was collected by suction filtration. The filtrate was evaporated to dryness and a second crop of product isolated (2 g; 6% yield; >99% e.e.). $^1$H NMR ($CDCl_3$) was consistent with the structure of the product.

(S)-N-Benzoylazetidine-2-carboxylic acid (5.90 g; 28.78 mmol) was dissolved in a solution of sodium hydroxide (6.92 g; 0.173 mol) in water (92 mL), at room temperature with stirring. The reaction was heated to 75° C. for 22 hours and then allowed to cool to room temperature. The reaction mixture was adjusted to pH 2 (c.HCl) and extracted with ethyl acetate (3×100 mL). The aqueous solution was then evaporated to dryness, yielding a white solid (13 g). This was slurried in absolute ethanol (150 mL) at 50° C. for 1 hour and then allowed to cool to room temperature (ca. 1 hour). The salt was removed by suction filtration and the ethanolic solution evaporated to dryness, yielding a white solid (1.85 g, 47% yield). The isolate was re-dissolved in water (100 mL) and neutralised by stirring with Amberlite IRA-67 ion exchange resin (5 g) for 30 minutes (to pH 7.1). The resin was removed by suction filtration and the filtrate evaporated to dryness, yielding a slightly off-white solid (1.38 g; quantitative yield). The off-white solid was slurried with refluxing MeOH (10 mL) for 5 minutes, allowed to cool to room temperature and the purified product collected by suction filtration (905 mg; 31% yield; 98% e.e.). $^1$H NMR ($D_2O$) was consistent with the structure of the product.

What is claimed is:

1. A process for obtaining an enantiomerically enriched N-acylazetidine-2-carboxylic acid comprising contacting a racemic N-acylazetidine-2-carboxylic acid ester with an enzyme that displays enantiospecificity to form enantiomerically enriched N-acylazetidine-2-carboxylic acid.

2. The process as claimed in claim 1, wherein the acyl group is optionally substituted benzoyl.

3. The process as claimed in claim 2, wherein the acyl group is benzoyl.

4. The process as claimed in claim 1, wherein the ester is a lower alkyl ester.

5. The process as claimed in claim 4, wherein the ester is a methyl ester.

6. The process as claimed in claim 1, the enzyme has enantiospecificity for the (5)-ester.

7. The process as claimed in claim 6, wherein the enzyme has properties characteristic of *Candida antarctica* lipase.

8. The process as claimed in claim 6, wherein the enzyme has properties characteristic of *Aspergillus tamarii* esterase.

9. The process according to claim 1, and further comprising crystallizing the N-acylazetidine-2-carboxylic acid from a solvent to increase the enantiomeric enrichment of the N-acylazetidine-2-carboxylic acid.

10. The process as claimed in claim 9, wherein the solvent is ethyl acetate.

11. The process according to claim 1, further comprising racemizing the unwanted enantiomer.

12. The process as claimed in claim 11, wherein the racemization is effected through treatment with a base.

13. The process as claimed in claim 12, wherein the base is sodium methoxide.

14. The process according to claim 1, further comprising the enantiomerically enriched N-acylazetidine-2-carboxylic acid.

15. The process as claimed in claim 14, wherein the deacylation is effected by hydrolysis in the presence of alkali.

16. The process as claimed in claim 15, wherein the alkali is an alkali metal hydroxide.

17. The process as claimed in claim 14, wherein the azetidine-2-carboxylic acid is (S)-azetidine-2-carboxylic acid.

18. A method of selection of an enzyme for use in a process according to claim 1, which method comprises the attempted biotransformation of a racemic N-acylazetidine-2-carboxylic acid ester in the presence of a test enzyme and determining whether or not an enantiomerically enriched N-acylazetidine-2-carboxylic acid is formed.

* * * * *